(12) United States Patent
Frisch

(10) Patent No.: US 7,018,534 B2
(45) Date of Patent: Mar. 28, 2006

(54) APPARATUS AND METHOD FOR CONTROLLING BIOMASS GROWTH IN SUSPENDED CARRIER BIOREACTOR

(75) Inventor: Samuel Frisch, Manalapan, NJ (US)

(73) Assignee: Shaw Environmental and Infrastructure, Inc., Lawrenceville, NJ (US)

( * ) Notice: Subject to any disclaimer, the term of this patent is extended or adjusted under 35 U.S.C. 154(b) by 106 days.

(21) Appl. No.: 10/682,624

(22) Filed: Oct. 9, 2003

(65) Prior Publication Data

US 2005/0077239 A1    Apr. 14, 2005

(51) Int. Cl.
*C02F 3/08*    (2006.01)

(52) U.S. Cl. .............. 210/616; 210/629; 210/150; 210/194; 210/220

(58) Field of Classification Search ........... 210/616, 210/617, 618, 627, 629, 150, 151, 194, 220
See application file for complete search history.

(56) References Cited

U.S. PATENT DOCUMENTS

| | | | | |
|---|---|---|---|---|
| 4,137,171 A | * | 1/1979 | Yokata .................... | 210/150 |
| 4,452,701 A | * | 6/1984 | Garrett et al. ............. | 210/627 |
| 4,454,038 A | * | 6/1984 | Shimodaira et al. ........ | 210/150 |
| 4,521,311 A | * | 6/1985 | Fuchs et al. ............... | 210/616 |
| 4,810,377 A | * | 3/1989 | Kato et al. ................. | 210/150 |
| 4,839,053 A | * | 6/1989 | Tharp ....................... | 210/616 |
| 5,372,712 A | * | 12/1994 | Petit ......................... | 210/618 |
| 6,077,424 A | * | 6/2000 | Katsukura et al. ......... | 210/151 |
| 6,616,845 B1 | * | 9/2003 | Shechter et al. ........... | 210/616 |

OTHER PUBLICATIONS

Eckenfelder, "Principles of Water Quality Management," 1980, pp. 216 and 218.*
Steel and McGhee, "Water Supply and Sewerage," 1979, pp. 503, 508 and 509.*
International Search Report, application No. PCT/US04/33248, dated Oct. 3, 2005.

* cited by examiner

*Primary Examiner*—Christopher Upton
(74) *Attorney, Agent, or Firm*—RatnerPrestia

(57) ABSTRACT

The present invention provides a bioreactor comprising a vessel having a bottom region and an interior configured to contain an aqueous suspension of biomass and media. A first gas outlet is provided at the bottom region of the vessel. The first gas outlet is positioned to introduce a first stream of gas to promote growth of the biomass on the media. A lift tube is disposed within the vessel, the lift tube having an inlet disposed at the bottom region of the vessel. A second gas outlet is disposed proximal the lift tube inlet to feed gas to the inlet of the lift tube.

20 Claims, 3 Drawing Sheets

APPARATUS AND METHOD FOR CONTROLLING BIOMASS GROWTH IN SUSPENDED CARRIER BIOREACTOR

FIELD OF THE INVENTION

The present invention relates to bioreactors, and more specifically, to the control of biomass growth on suspended media within fluidized-bed bioreactors.

BACKGROUND OF THE INVENTION

Biological reactors find increasing use in many areas of industry, including waste treatment plants. Efforts to protect the environment include advanced biological treatment of wastewater through the use of biological reactors, and in particular, fluidized-bed bioreactors. It is the activity of biologically active materials (or "biomass") within the biological reactor that degrades contaminants in the influent to effect a filtration process. As the biomass treats, through enzymatic reaction, these contaminants, the biomass grows through reproduction within the system. Typically this activity occurs within a treatment vessel which contains media or other substrate material or carriers on which the biomass attaches and grows as contaminants are consumed. Typical media would include plastic beads, resin beads, sand, or ion exchange resins, among other carriers.

Conventional fluidized-bed bioreactors, such as a well-mixed suspended carrier reactors (SCRs), suffer from operational drawbacks in that the media or carriers of the fluidized bed may be subject to excessive buildup of biomass and precipitates, thereby causing compromised flow distribution, excessive media and/or biomass carryover, crusting, increased clogging of filters, and the like. If not properly limited, biomass and precipitate buildup is detrimental to system performance. Uncontrolled biomass film growth in a fluidized bed biological reactor can also result in an undesirable loss of media.

Media bed expansion can, under certain circumstances, be limited by the application of shear, but the success of such a control strategy depends upon whether excess biomass and suspended solids can be transported to the top of the fluidized bed. More specifically, it is recognized that such transportation of excess biomass and suspended solids toward the top of the bed is promoted by several dominant mechanisms. For example, media grains that are coated with thicker layers of biomass tend to have an overall particle density that is less than the average particle density within the fluidized bed. Those particles, therefore, are transported to the top of the fluidized bed by virtue of upward moving fluid flow as well as the reduced particle density. This upward movement results in some shear forces acting on biomass-covered particles which does separate some biomass from its supportive media.

One solution to this problem has been to increase the amount and size of cavities introduced into the system to increase the shear and subsequent separation of the biomass from its media. An example of a bioreactor in which such a system is operated is shown in FIG. 1.

FIG. 1 illustrates vessel 100 which contains an aqueous suspension of biomass and media, such as would be used in a waste-water treatment plant. Vessel 100 is fed by inlet pipe 105 with a waste-water stream. The biomass covered media 101 is shown as relatively small dots, and air introduced into the system is shown as cavities 110. (Some would say bubbles. For purposes of this disclosure, however, it is intended that bubble and cavity be used interchangeably). In FIG. 1, cavities 110 are shown as roughly spherical cavities of gas which travel upward through the liquid contained in vessel 100. Typically the gas is air, although it could be a gas having an oxygen enriched content (as compared to air) or even be pure oxygen. Air sparger 120 is shown at the bottom of vessel 100 and is fed air (in a typical embodiment) from line 125. Air sparger 120 in this conventional embodiment would be a coarse diffuser to create relatively large cavities and thus increase the shear forces acting on the biomass covered media. These cavities of air thus produced travel upward through the liquid in vessel 100.

The introduction of air into the liquid via air sparger 120 serves two purposes. First, it supplies oxygen which is needed for the enzymatic reactions which are taking place in the system as contaminants are removed and biomass is formed on the media. Secondly, the upward cavity movement causes currents to be developed in the liquid. These currents will cause movement of the media and the application of shear stresses to the media and biomass. This interaction between pieces of media with other pieces of media, fluid, biomass, and the interior wall(s) of vessel 100 results in collisions which cause: (1) contact between the microorganisms and suspended organic matter, and (2) accumulated biomass to break free from its respective supportive media. This freed biomass will typically rise to the top of the vessel as its density is less than that of the liquid system. FIG. 1 shows a filter 140 which is used to filter out the biomass as "clean" effluent water is drawn from the system through outlet pipe 150.

Many of these types of systems rely on the energy and resultant shear of the cavities to separate the biomass from the media. Typically, however, the amount of energy that must be input into the system through the introduction of the cavities to achieve adequate shear and subsequent separation far exceeds that which is necessary to delivery adequate oxygen for enzymatic reaction. In other words, the majority of the energy input into a conventional system is used to separate biomass from the media, as compared to a minority which is used to supply the necessary oxygen.

Thus, there remains a need in the industry for a more energy-efficient and cost-efficient system for separating accumulated biomass from a slurry of a fluidized-bed bioreactor to inhibit uncontrolled biomass growth and precipitate accumulation. It is therefore an object of the present invention to provide a system for controlling biomass growth while reducing capital and energy costs. Other objects and advantages of the invention will become apparent to those skilled in the art from the drawings, the detailed description of preferred embodiments, and the appended claims.

SUMMARY OF THE INVENTION

The present invention provides a bioreactor comprising a vessel having a bottom region and an interior configured to contain an aqueous suspension of biomass and media. A first gas outlet is provided at the bottom region of the vessel. The first gas outlet is positioned to introduce a first stream of gas to promote growth of the biomass on the media. A lift tube is disposed within the vessel, the lift tube having an inlet disposed at the bottom region of the vessel. A second gas outlet is disposed proximal the lift tube inlet to feed gas to the inlet of the lift tube.

Also included as a part of the present invention is a method for promoting biomass growth and separating biomass from the media. The method includes introducing a first stream of gas into the bioreactor to promote the growth of biomass on the media. A second stream of gas is introduced into the bioreactor near an inlet of a lift pipe to generate sufficient shear forces to separate biomass from the media.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

As discussed above, typical air sparging which would occur in a fluidized-bed bioreactor achieves two effects. It introduces oxygen needed for enzymatic reaction and also causes mixing and interaction within the system between system components. This intended mixing aids in oxygen mass transfer (the first effect), as well as biomass growth control through the introduction of shear forces via turbulent flow interaction between media and other parts of the system. Thus, the amount of energy and oxygen which needs to be entered into the system is determined by achieving sufficient results of both objectives. It is the later factor, however (as opposed to oxygen mass transfer), which typically drove the amount of air or other gas that needed to be pumped into the system. In other words, the amount of air pumped into the system to cause sufficient liquid disturbance to achieve at least a minimum amount of biomass accumulation control was determinative of the air flow rate into the system. Oxygen mass transfer was more typically the less-dominant variable in the consideration of minimum air delivery requirements.

The present invention provides an apparatus and method, however, to reduce the total amount of air (or oxygenated gas) which is needed to be added to a given system as compared to the prior art. The present invention takes advantage of a combination of two or more different gas sources, or two or more outlets from a single gas source, to achieve an overall more efficient process. As described in more detail below, the present invention takes advantage of a lift tube disposed within the vessel which has its own gas outlet disposed at or near the lift tube inlet toward the bottom of the vessel to feed gas directly to the lift tube. This allows an overall reduction in the amount of gas which must be delivered to the vessel as compared to the prior art (as well as a concomitant reduction in associated costs such as energy, maintenance, etc.).

Figure 2:
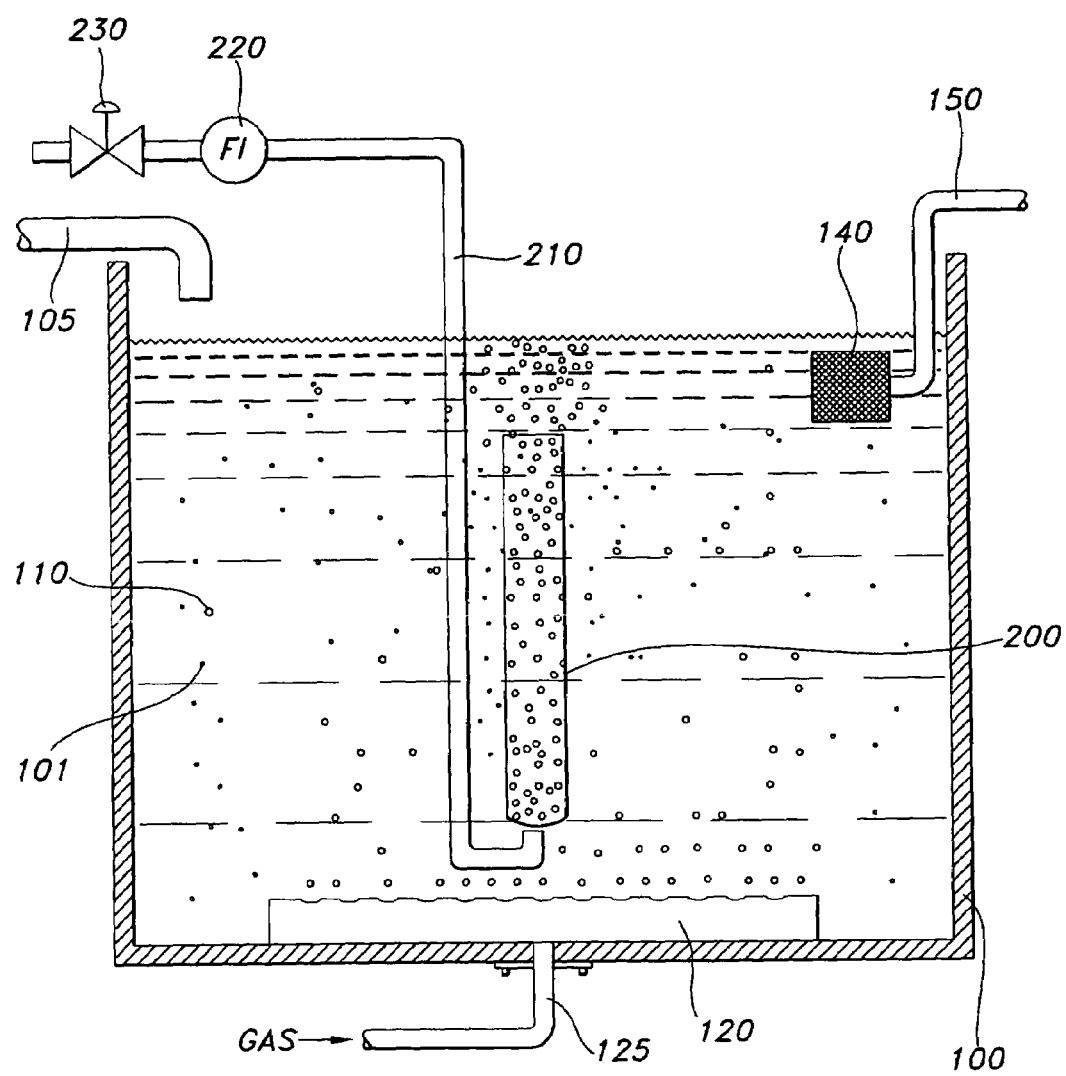
FIG. 2 schematically shows an embodiment of the present invention with one lift tube.

FIG. 2 shows an embodiment of the present invention in which lift tube 200, which has an open bottom and an open top, is disposed within vessel 100. Lift tube 200 is fed gas from line 210. Though not shown in FIG. 2, a gas source optionally feeds gas to the lift tube 200 at a location near or proximal to the inlet at the base of the lift tube 200. More specifically, according to one embodiment, the gas is delivered through a hose or tube or other conduit coupled to lift tube 200 by means of a tubing adapter fitting threaded into the side of the lift tube 200. Other arrangements are contemplated as well to provide a lift action for materials within the lift tube 200. Flow indicator 220 and valve 230 are preferably used to control gas flow into lift tube 200. Support for lift tube 200 is not shown in the schematic, partial cross-section view, but could come in any number of ways known to those skilled in the art.

Figure 1:
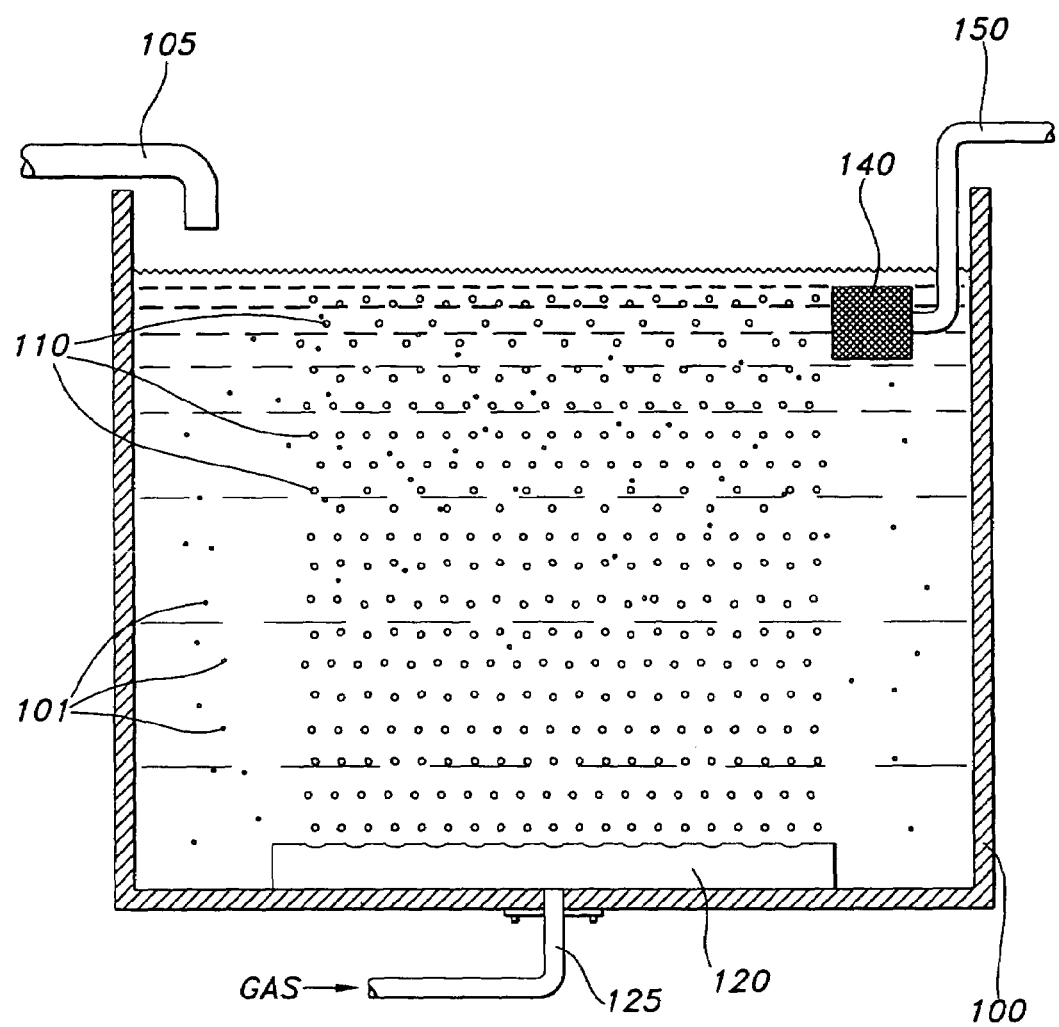
FIG. 1 schematically shows an embodiment according to the prior art.

Air sparger 120 shown in FIG. 2 is, for example, a fine bubble aerator. As is shown in FIG. 2, the total flow of gas resulting from the sum of the cavities 110 ascending the fluid in vessel 100 that are formed from air sparger 120 is much less than the flow of gas resulting from the sum of cavities 110 ascending from air sparger 120 in FIG. 1. This is because the necessary biomass separation due to shear forces is accomplished in lift tube 200, in which cavities are formed from line 210. It is this shear force separation occurring in lift tube 200 which allows for a reduction in gas input through sparger 120.

It has been discovered that an overall reduction in air flow into vessel 100 can be achieved where lift tube 200 is employed, as compared to the prior art which did not use a lift tube in conjunction with a sparger. For example, if X is the total amount of air which is pumped into the system of FIG. 1 to treat Y gallons of waste water per hour, it can be seen that X cubic feet per minute (cfm) would enter through line 125 and pass through air sparger 120. Taking the same Y requirement for the system of FIG. 2, however, and noting that air will be introduced into the vessel of FIG. 2 through line 125 at a rate of A cfm and through line 210 at a rate of B cfm, it has been discovered that the following relationship can be achieved: $X > A + B$.

This reduction in the amount of air needed is likely due to the fact that shear forces are more effective at separating biomass from media in lift tube 200 because of the decreased flow area under which shear forces act as compared to allowing them to occur only throughout the vessel itself. In other words, lift tube 200 makes it possible to yield a higher separation efficiency. As noted above, because the shear force separation element of gas introduction is the primary factor in air flow rate determinations into a given system (as compared to oxygen delivery), the result of the use of the lift tube is that less overall air is needed for the system to perform.

Another factor which increases biomass separation from media in the system through the use of lift tube 200 is that larger cavities (larger diameter bubbles) can be used to cause the necessary shear force interaction than can be used where the cavities are supplied for both shear force interaction and oxygen delivery. In other words, line 210 can supply larger cavities into lift tube 200 for purposes of biomass separation and to provide for high flow within a smaller area, as compared to the smaller diameter cavities which are created at air sparger 120 for purposes of oxygen mass transfer. This also allows for a reduction in overall gas supply to the system. To take advantage of this aspect of the present invention, fine bubble aerators can be used at one or both gas outlets. In an exemplary embodiment, a fine bubble aerator is used for oxygen mass transfer while no aerator is used for lift purposes.

Fine bubble aerators, used to create different sized cavities or bubbles, are known to those skilled in the art. For example, fine bubble aerators are available under the brand SANITAIRE from Water Pollution Control Corporation of Brown Deer, Wis.

Typically, fine bubbles are defined as cavities having a diameter of about 2 mm or less, preferably about 1 mm or less, and coarse bubbles are defined as cavities having a diameter larger than about 2 mm. Most typically, coarse bubbles have an average diameter between about 2–5 mm. Fine bubble aerators operate more efficiently than coarse bubble aerators. This is generally because there is a greater surface area of air/liquid interface per unit volume of the system with smaller bubbles as compared to larger bubbles. Specifically, looking at bubbles with two different diameters under the same total volume gas flow rate, the ratio of the total surface areas is inversely proportional to the ratio of the diameters. For example, for the same overall air flow rate into a liquid tank, decreasing the bubble diameters from 2.5 mm to 0.5 mm would increase the interfacial contact area between the air and water by a factor of five for spherical bubbles. Without the benefit of the present invention, coarse bubble aerators would have to be used and that would lead to a less efficient system. The present invention allows a reduction in capital and operating costs. For example, pump sizing is reduced from 100 h.p. for the case of a coarse bubble aerator to 60 h.p. for a fine bubble aerator.

Still another aspect of the present invention is the use of a plurality of lift tubes within the same vessel. A plurality, such as 2 or more small lift tubes, disposed within the vessel, each with its own air source, can further take advantage of the overall reduction in air delivery to the vessel while still maintaining biomass growth control and good system performance. An example of a vessel having two lift tubes is shown in FIG. 3.

Figure 3:
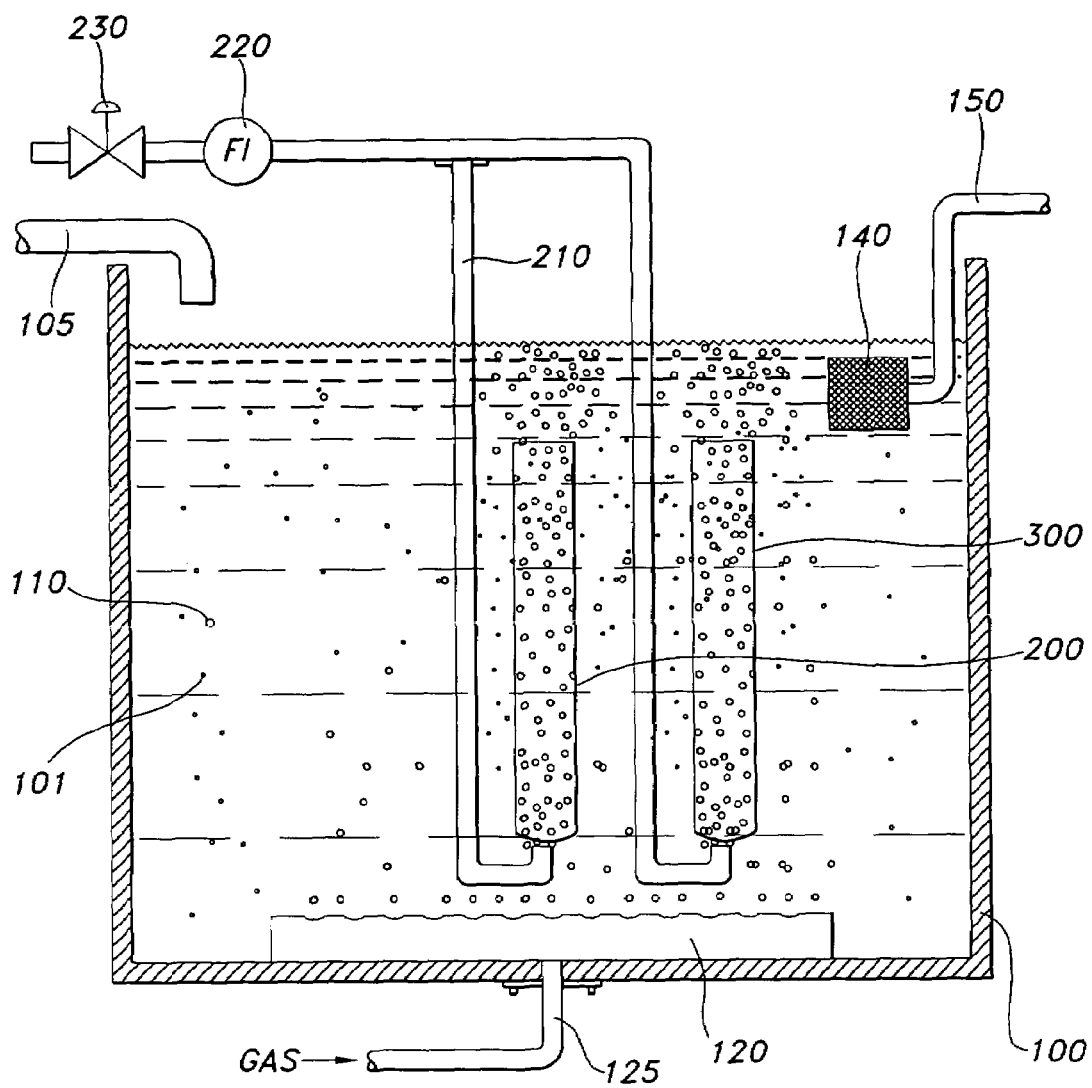
FIG. 3 schematically shows an alternative embodiment of the present invention with two lift tubes.

FIG. 3 shows the same flow indicator 220 and valve 230 controlling both lift tubes 200 and 300. Also, a pressure indicator is optionally provided between the flow indicator and valve, wherein the flow indicator, valve, and pressure indicator together form a control assembly for the control of gas flow. Although a single control assembly can be utilized to control the flow of gas to both outlets, separate control schemes or control assemblies could also be used to control the flow of gas toward each gas outlet (not shown).

Another aspect of the present invention is the use of the disclosed apparatus in a novel method for achieving efficient bioreactions. A preferred method generally comprises the steps of introducing a first stream of gas into a bioreactor through an air sparger to promote the growth of biomass on media within the liquid contents of the bioreactor, and also introducing a second stream of gas into the bioreactor at a bottom region of a lift pipe to produce a turbulent, upward flow of media and liquid through the lift pipe with sufficient shear forces to break accumulated biomass from the media. As noted above, the overall amount of gas and energy needed to operate this method is less than the situation where only an air sparger is used to provide for both oxygen delivery and shear force creation.

In a preferred embodiment, the first stream of gas introduced through the air sparger comprises passing the gas through a fine bubble aerator. Preferably, the method operates by passing air into the bioreactor, although oxygen enriched air or even pure oxygen could be used. In a typical application of the present method, the bioreactor is used to treat waste water, whereby a stream of contaminated water or sewage is introduced into the vessel and after sufficient enzymatic activity is allowed to occur, a purified water stream from the bioreactor is removed.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A bioreactor comprising:
    a vessel having a bottom region and an interior configured to contain an aqueous suspension of biomass and media;
    a first gas outlet at the bottom region of the vessel, said first gas outlet positioned to introduce a first stream of gas providing a first plurality of cavities to promote growth of said biomass on said media;
    a lift tube disposed within the vessel, the lift tube having an inlet disposed at the bottom region of the vessel; and
    a second gas outlet positioned to feed gas into the lift tube at a location proximal to the inlet of the lift tube, said second gas outlet configured to introduce a second stream of gas providing a second plurality of cavities to promote separation of said biomass from said media in said lift tube,
    wherein said second gas outlet is configured to introduce cavities larger than said cavities introduced by said first gas outlet.

2. The bioreactor of claim 1 wherein there is a plurality of lift tubes disposed within the vessel.

3. The bioreactor of claim 1 wherein the first gas outlet comprises a fine bubble aerator.

4. The bioreactor of claim 1 further comprising at least one gas source connected to deliver gas to the first gas outlet, to the second gas outlet, or to the first gas outlet and the second gas outlet.

5. The bioreactor of claim 4 wherein the gas is air.

6. The bioreactor of claim 4 wherein the gas is oxygen.

7. The bioreactor of claim 1 wherein the vessel is configured to receive waste water from a source of waste water.

8. The bioreactor of claim 1 wherein the lift tube is oriented substantially vertically within the vessel.

9. In a bioreactor containing biomass and media, a method for promoting biomass growth and separating biomass from the media, said method comprising the steps of:
    introducing a first stream of gas providing a first plurality of cavities into the bioreactor to promote the growth of biomass on the media; and
    introducing a second stream of gas providing a second plurality of cavities into the bioreactor near an inlet of a lift pipe to generate sufficient shear forces to separate biomass from the media,
    wherein the second stream of gas introduces cavities larger than said cavities introduced by the first stream of gas.

10. The method of claim 9 wherein the step of introducing the first stream of gas is performed through an air sparger.

11. The method of claim 10 wherein the step of introducing the first stream of gas comprises passing the gas through a fine bubble aerator.

12. The method of claim 9 wherein the steps of introducing the first stream of gas and the second stream of gas comprise introducing the first stream of gas and the second stream of gas from a gas source.

13. The method of claim 9 wherein at least one of the introducing steps comprises introducing air.

14. The method of claim 9 wherein at least one of the introducing steps comprises introducing oxygen.

15. The method of claim 9 further comprising the step of treating waste water in the bioreactor.

16. The method of claim 9 further comprising the step of adding a contaminated waste water stream into the vessel before introducing the first and second streams of gas.

17. The method of claim 16 further comprising the step of removing a purified water stream from the bioreactor after sufficient gas has been introduced to the bioreactor that the contaminants have been reduced.

18. In a bioreactor comprising a vessel having an interior configured to contain an aqueous suspension of biomass and media and a lift tube having an inlet, a method comprising the steps of:
   introducing a first stream of gas providing a first plurality of cavities into the bioreactor to promote the growth of the biomass on the media; and
   introducing a second stream of gas providing a second plurality of cavities into the inlet of the lift tube to generate shear forces to separate the biomass from the media,
   wherein the second stream of gas introduces cavities larger than said cavities introduced by the first stream of gas.

19. The method of claim 18 wherein the step of introducing the first stream of gas comprises passing the gas through a fine bubble aerator.

20. The method of claim 18 wherein the steps of introducing the first stream of gas and the second stream of gas comprise introducing the first stream of gas and the second stream of gas from a gas source.

* * * * *